United States Patent [19]

Strasser et al.

[11] Patent Number: 5,411,955
[45] Date of Patent: May 2, 1995

[54] THIADIAZINECARBOXAMIDE DERIVATIVES, PROCESSES FOR THEIR PREPARATION AND PHARMACEUTICALS

[75] Inventors: Rupert Strasser, Strasslach; Peter Zeiller; Rainer J. Klauser, both of Munich, all of Germany

[73] Assignee: Luitpold Pharma GmbH, Munich, Germany

[21] Appl. No.: 104,115

[22] PCT Filed: Dec. 11, 1992

[86] PCT No.: PCT/DE92/01048

§ 371 Date: Sep. 16, 1993

§ 102(e) Date: Sep. 16, 1993

[87] PCT Pub. No.: WO93/12119

PCT Pub. Date: Jun. 24, 1993

[30] Foreign Application Priority Data

Dec. 13, 1991 [DE] Germany .................. 41 41 218.4

[51] Int. Cl.⁶ .................. A61K 31/54; C07D 513/04
[52] U.S. Cl. .................. 514/214; 514/222.5; 514/222.8; 540/578; 544/8; 544/10
[58] Field of Search .................. 544/8, 10; 514/222.5, 514/222.8, 214; 540/578

[56] References Cited

U.S. PATENT DOCUMENTS

| | | | |
|---|---|---|---|
| 2,956,997 | 10/1960 | Teufel | 260/243 |
| 3,203,954 | 8/1965 | Wright | 260/243 |
| 3,223,703 | 12/1965 | Wright | 260/243 |
| 3,591,584 | 7/1971 | Lombardino | 260/243 |
| 4,450,269 | 5/1984 | Peake et al. | 544/8 |

FOREIGN PATENT DOCUMENTS

| | | |
|---|---|---|
| 0001113 | 9/1977 | European Pat. Off. . |
| 8601216 | 3/1984 | Spain . |

OTHER PUBLICATIONS

Goya et al, "1-2-6-Thiadiazine-3,5(2H,6H)—dione 1,1-dioxide Derivatives: Crystal Structure, Physico-chemical and Biological Properties" *Can J. Chem.*. vol. 65, 1987, pp. 298-302.
Journal of Medicinal Chemistry, vol. 14, No. 12, Dec. 1971. Lombardino et al pp. 1171-1175.
Journal of Medicinal Chemistry, vol. 16, No. 5, May 1973. Lombardino et al. pp. 493-494.
Chemical Abstracts, vol. 109, No. 15, Oct. 1988. 109:129066z.
J. Chem. Research (S), 1988, 94-95, Elguero et al, "Proton and Carbon-13 N.M.R. and Crystallographic Study of Substituted 1,2,6-Thiadiazinones: Comparison with Related Pyrazoles".
J. Org. Chem. 29, (1964) 1905-1909, Wright, "The Reaction of Sulfamide with α-and β-Diketones. The Preparation of 1,2,5-Thiadiazole 1,1-Dioxides and 1,2,6-Thiadiazine 1,1-Dioxides".
Chemical Abstracts, vol. 55, No. 9, May 1961, 8446f-8448a, Teufel, "Substituted 3,5-Dioxotetrahydro-1,26-Thiadiazine 1,1-Dioxides".
Chemical Abstracts, vol. 104, No. 23, Jun. 1986, 2077234r, Goya et al, "Synthesis and Pharmacological Assay of 1,2,6-thiadiazine Derivatives Related to Phenylbutazone".
Chemical Abstracts, vol. 106, No. 1, Jan. 1987, 5093z, Goya et al, "Thienothiadiazinone Dioxides".
Chemical Abstracts, vol. 107, No. 11, Sep. 1987, 89296z, Goya et al, "1-2-6-Thiadiazine-3,5(2H,6H)-dione 1,1-dioxide derivatives: Crystal Structure, Physiochemical and Biological Properties".

*Primary Examiner*—Mukund J. Shah
*Assistant Examiner*—Matthew V. Grumbling
*Attorney, Agent, or Firm*—Burns, Doane, Swecker & Mathis

[57] ABSTRACT

The invention relates to thiadiazinecarboxamide derivatives of the general formula I

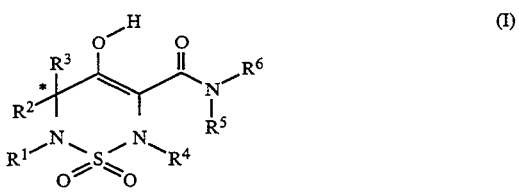

to processes for their preparation, and to pharmaceuticals comprising them.

13 Claims, No Drawings

THIADIAZINECARBOXAMIDE DERIVATIVES, PROCESSES FOR THEIR PREPARATION AND PHARMACEUTICALS

DESCRIPTION

The invention relates to compounds of the general formula I

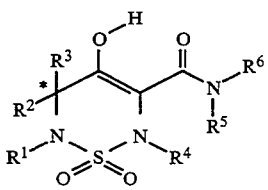

in which $R^1$ denotes a lower alkyl radical, an aryl radical, a heteroaryl radical or an aryl-lower-alkyl radical, $R^2$ denotes a hydrogen atom, a lower alkyl radical or an aryl radical, $R^3$ denotes a hydrogen atom, a lower alkyl radical, an aryl radical, a heteroaryl radical, an aryl-lower-alkyl radical or a saturated, unbranched $C_1$-$C_4$-alkyl radical which is monosubstituted by a radical selected from the group consisting of —$OR^7$, —$NR^8R^9$, —CO—$OR^{10}$, —$SR^{11}$, —CO—$NR^{12}R^{13}$ or —N-H—C(NH_2) (=NH), or in which $R^1$ and $R^3$ together form an unbranched, saturated alkylene radical having two, three, four or five carbon atoms and thus, together with the adjacent nitrogen atom and carbon atom of the thiadiazine ring system, form a ring having four, five, six or seven ring members, $R^4$ denotes a hydrogen atom, a lower alkyl radical or an aryl-lower-alkyl radical, $R^5$ denotes a hydrogen atom or a lower alkyl radical, $R^6$ denotes a hydrogen atom, a lower alkyl radical, an aryl radical, a heteroaryl radical or an aryl-lower-alkyl radical, $R^7$, $R^8$, $R^9$, $R^{10}$, $R^{11}$, $R^{12}$ and $R^{13}$ independently of one another denoting a hydrogen atom, a lower alkyl radical, an aryl radical or an aryl-lower-alkyl radical, and salts thereof with the physiologically acceptable acids and bases, the abovementioned term aryl radical denoting phenyl radical, a 1-naphthyl radical or a 2-naphthyl radical, each of which is optionally substituted by one, two or three identical or different substituents selected from the group of the halogen atoms, hydroxyl radicals, lower alkyl radicals, lower alkyloxy radicals, carboxyl radicals, lower alkyloxycarbonyl radicals, nitro groups, sulfo radicals, trifluoromethyl radicals or hydrogen-atom- or lower-alkyl-radical-substituted amino groups, and the abovementioned term heteroaryl radical denoting one of the following radicals: furanyl radicals, thienyl radicals, pyrrolyl radicals, pyrazolyl radicals, imidazolyl radicals, triazolyl radicals, thiazolyl radicals, oxazolyl radicals, isothiazolyl radicals, isoxazolyl radicals, thiadiazolyl radicals, pyridyl radicals, pyrimidyl radicals, pyrazinyl radicals, triazinyl radicals, benzofuranyl radicals, benzothienyl radicals, indolyl radicals, benzoxazolyl radicals, benzothiazolyl radicals, benzimidazolyl radicals, quinolinyl radicals or isoquinolinyl radicals, it being possible for the abovementioned radicals to be linked to the basic structure of the compounds of the general formula I via each ring carbon atom and it being possible for the abovementioned rings to be optionally substituted by one or two identical or different substituents selected from the group of the halogen atoms, hydroxyl radicals, lower alkyl radicals, lower alkyloxy radicals, carboxyl radicals, lower alkyloxycarbonyl radicals, nitro groups, sulfo radicals, trifluoromethyl radicals or hydrogen-atom or lower-alkyl-radical-substituted amino groups, and the abovementioned term aryl-lower-alkyl radical denoting a methyl radical or an ethyl radical each of which is substituted by an aryl radical as defined above, and the abovementioned term lower alkyl radical, or the term "lower alkyl" in connection with lower alkyloxy radical or lower alkyloxycarbonyl radical denoting an unbranched or branched saturated hydrocarbon radical having up to six carbon atoms.

In general, the compounds of the general formula I according to the invention exist individually in the sense of keto-enol tautomerism or in the form of mixture.

The following explanations apply to the various substituents or radicals in formula I which have been mentioned in connection with the present application:

Examples of lower alkyl radicals are methyl radicals, ethyl radicals, n-propyl radicals, iso-propyl radicals, n-butyl radicals, iso-butyl radicals, 1-methylpropyl radicals, tert.-butyl radicals, n-pentyl radicals, 1-methylbutyl radicals, 2-methylbutyl radicals, 3-methylbutyl radicals, 1,1-dimethylpropyl radicals, 2,2-dimethylpropyl radicals, 1,2-dimethylpropyl radicals, 1-ethylpropyl radicals, n-hexyl radicals, 1-methylpentyl radicals, 2-methylpentyl radicals, 3-methylpentyl radicals, 4-methylpentyl radicals, 1,1-dimethylbutyl radicals, 2,2-dimethylbutyl radicals, 3,3-dimethylbutyl radicals, 1,2-dimethylbutyl radicals, 2,3-dimethylbutyl radicals, 1,3-dimethylbutyl radicals, 1-ethylbutyl radicals, 2-ethylbutyl radicals, 1,1,2-trimethylpropyl radicals, 1,2,2-trimethylpropyl radicals, 1-ethyl-2-methylpropyl radicals or 1-ethyl-1-methylpropyl radicals. Preferred in this context are methyl radicals, ethyl radicals, n-propyl radicals, iso-propyl radicals, n-butyl radicals, iso-butyl radicals, tert.-butyl radicals, 2,2-dimethylpropyl radicals or 1-methylpropyl radicals. Particularly preferred are methyl radicals, ethyl radicals, iso-propyl radicals and n-butyl radicals.

Examples of aryl radicals are phenyl radicals, 1-naphthyl radicals and 2-naphthyl radicals, each of which can optionally have one, two or three identical or different constituents in all positions of the aromatic ring system which are possible. Preferred aryl radicals are phenyl radicals which can optionally have one, two or three identical or different substituents in all positions of the aromatic ring system which are possible. Examples of substituents are halogen atoms, hydroxyl radicals, lower alkyloxy radicals, carboxyl radicals, lower alkyloxycarbonyl radicals, lower alkyl radicals, nitro groups, sulfo radicals, trifluoromethyl radicals or hydrogen-atom- or lower-alkyl-radical substituted amino groups. Preferred substituents are halogen atoms, lower alkyl radicals, lower alkyloxy radicals, lower alkyloxycarbonyl radicals and trifluoromethyl radicals. Particularly preferred aryl radicals are phenyl radicals, 2-methylphenyl radicals, 4-methylphenyl radicals, 2-methoxyphenyl radicals, 4-methoxyphenyl radicals, 2-methoxy-5-methyl radicals, 2,3-dimethoxyphenyl radicals, 2,4-dimethoxyphenyl radicals, 2,5-dimethoxyphenyl radicals, 2,6-dimethoxyphenyl radicals, 3,4-dimethoxyphenyl radicals, 3,5-dimethoxyphenyl radicals, 2-ethoxyphenyl radicals, 4-ethoxyphenyl radicals, 2-chlorophenyl radicals, 4-chlorophenyl radicals, 2,4-dichlorophenyl radicals, 2,6-dichlorophenyl radicals, 2-fluorophenyl radicals, 4-fluorophenyl radicals or 3-trifluoromethylphenyl radicals. Very particularly preferred aryl radicals are phenyl radicals, 2-methoxyphenyl radicals, 4-methoxyphenyl radicals, 2-methoxy-5-methyl radicals, 2,4-dimethoxyphenyl radicals, 2,5-dimethoxyphenyl radicals, 4-ethoxyphenyl radicals, 4-chlorophenyl radicals, 4-fluorophenyl radicals or 3-trifluoromethylphenyl radicals.

Aryl-lower-alkyl radicals are methyl radicals or ethyl radicals which are substituted by an aryl radical defined as above. Preferred aryl-lower-alkyl radicals are benzyl radicals and phenyl ethyl radicals which are unsubstituted or monosubstituted or disubstituted on the phenyl ring by halogen atoms, lower alkyl radicals, lower alkyloxy radicals, trifluoromethyl radicals or lower alkyloxycarbonyl radicals. Particularly preferred aryl-lower-alkyl radicals are benzyl radicals, phenylethyl radicals, 2-methylbenzyl radicals, 4-methylbenzyl radicals, 2-methoxybenzyl radicals, 4-methoxybenzyl radicals, 2-ethoxybenzyl radicals, 4-ethoxybenzyl radicals, 2-fluorobenzyl radicals, 4-fluorobenzyl radicals, 2-chlorobenzyl radicals, 4-chlorobenzyl radicals, 2,4-dimethoxybenzyl radicals, 2,5-dimethoxybenzyl radicals, 2,4-dichlorobenzyl radicals, 2,6-dichlorobenzyl radicals, 2-trifluoromethylbenzylradicals, 3-trifluoromethylbenzyl radicals, 4-trifluoromethylbenzyl radicals, 4-methoxycarbonylbenzyl radicals or 4-ethoxycarbonylbenzyl radicals. Very particularly preferred aryl-lower-alkyl radicals are benzyl radicals, phenylethyl radicals, 2-methoxybenzyl radicals, 4-methoxybenzyl radicals, 2-ethoxybenzyl radicals, 4-ethoxybenzyl radicals, 4-fluorobenzyl radicals or 4-chlorobenzyl radicals.

Heteroaryl radicals are five-membered or six-membered aromatic heterocycles having one, two or three identical or different hetero atoms, such as nitrogen atoms, oxygen atoms or sulphur atoms, a benzene ring optionally being fused at any desired site and it being possible for the heteroaryl radicals to be unsubstituted or substituted by one or two identical or different substituents such as halogen atoms, hydroxyl radicals, lower alkyloxy radicals, carboxyl radicals, lower alkyloxycarbonyl radicals, lower alkyl radicals, nitro groups, sulfo radicals, trifluoromethyl radicals or hydrogen-atom- or lower-alkyl-radical-substituted amino groups and it being possible for the heteroaryl radicals to be linked via all ring carbon atoms to the basic structure of the compounds of the general formula I. Preferred heteroaryl radicals are the radicals mentioned below which can be unsubstituted or monosubstituted by halogen atoms, lower alkyl radicals, lower alkyloxy radicals or nitro groups: furanyl radicals, thienyl radicals, pyrrolyl radicals, pyrazolyl radicals, imidazolyl radicals, triazolyl radicals, thiazolyl radicals, oxazolyl radicals, isothiazolyl radicals, isoxazolyl radicals, thiadiazolyl radicals, pyridyl radicals, pyrimidyl radicals, pyrazinyl radicals, triazinyl radicals, benzofuranyl radicals, benzothienyl radicals, indolyl radicals, benzoxazolyl radicals, benzothiazolyl radicals, benzimidazolyl radicals, quinolinyl radicals or isoquinolinyl radicals, it being possible for the above-mentioned radicals to be linked via each ring carbon atom to the basic structure of the compounds of the general formula I. Particularly preferred are the following heteroaryl radicals: 2-furanyl radicals, 2-thienyl radicals, 3-thienyl radicals, 2-imidazolyl radicals, 2-thiazolyl radicals, 2-pyridyl radicals, 4-pyridyl radicals, 2-pyrimidyl radicals, 3-isoxazolyl radicals, 5-chloro-2-pyridyl radicals, 5-methyl-2-pyridyl radicals, 5-nitro-2-pyridyl radicals, 5-methyl-3-isoxazolyl radicals, 5-methyl-2-thiazolyl radicals and 6-methoxy-2-benzothiazolyl radicals. Very particularly preferred heteroaryl radicals are 2-pyridyl radicals, 2-thiazolyl radicals, 5-methyl-2-thiazolyl radicals or 5-methyl-3-isoxazolyl radicals.

Examples of halogen atoms are fluorine, chlorine, bromine and iodine atoms.

If the compounds according to the invention are in salt form, then these salts are the salts of the physiologically acceptable inorganic or organic bases or acids.

Examples of salts with physiologically acceptable bases are ammonium, sodium, potassium, lithium, magnesium and calcium salts and also salts with ethanolamine, triethanolamine, morpholin or piperidine.

Examples of salts with physiologically acceptable acids are citrate-, tartrate-, acetate-, fumarate-, gluconate-, glutamate-, lactate-, malate-, maleate-, mesylate-, succinate-, carbonate-, bicarbonate-, bisulphate-, phosphate-, hydrogenphosphate-, diphosphate-, chloride- and bromide-containing salts.

Unless $R^2$ and $R^3$ are identical radicals, the compounds according to the invention have the carbon atom designated with * as optically active centre and can be in the form of optically pure enantiomers in the D form or in the L form or as a racemate.

The compounds of the general formula I are synthesised analogously to methods known from the literature.

The invention therefore also relates to a process for the preparation of compounds of the general formula I which is characterised in that a compound of the general formula II

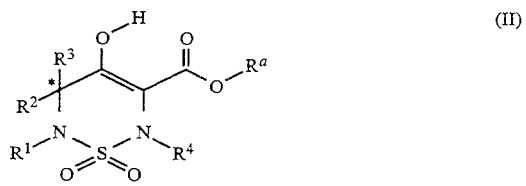

(II)

in which $R^1$, $R^2$, $R^3$ and $R^4$ are as defined in claim 1 and $R^a$ denotes a methyl or ethyl radical, are reacted in a manner known per se with an amine of the general formula III $R^5R^6NH$ (III)

in which $R^5$ and $R^6$ are as defined in claim 1.

The known syntheses below are to be mentioned by way of example only.

Step 1

α-Amino acid esters, preferably methyl and ethyl esters, and salts thereof, are prepared by conventional methods (for example K.-H. Deimer, P. Thamm, P. Stelzel in Houben-Weyl, Methoden der Organischen Chemie [Methods in Organic Chemistry], Volume 15, part 1, p. 315 et seq., Georg Thieme Verlag, Stuttgart 1974) from α-amino acids, for example by the following equation:

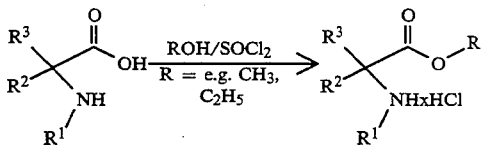

The preparation of α-amino acids which are substituted on the nitrogen atom by R¹ is known, as is the synthesis of the various unnatural amino acids which are substituted on the α-carbon atom by R² and/or R³ (for example Th. Wieland in Houben-Weyl, Methoden der Organischen Chemie [Methods in Organic Chemistry], Volume XI, part 2, p. 305 et seq., Georg Thieme Verlag, Stuttgart 1958).

Step 2

The reaction of chlorosulphonyl isocyanate with benzyl alcohol followed by a reaction with α-amino acid esters or with α-amino acid ester hydrochlorides using tertiary amino bases gives N-[N'-(benzyloxycarbonyl)sulphamoyl]-α-amino acid esters.

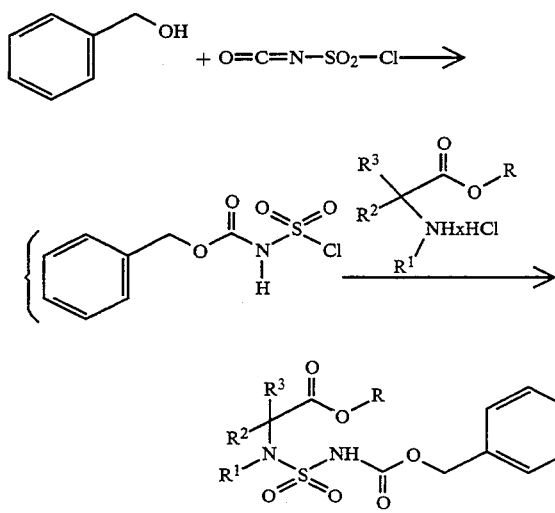

Step 3

Subsequent catalytic hydrogenation gives the correspondingly unsubstituted N-sulphamoyl-α-amino acid esters.

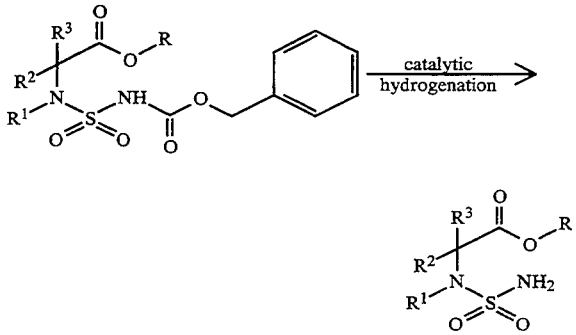

Step 4

Using sodium methanolate, cyclisation is effected by heating with elimination of ROH to give the corresponding 1,1-dioxo-1,2,5-thiadiazolidin-3-one.

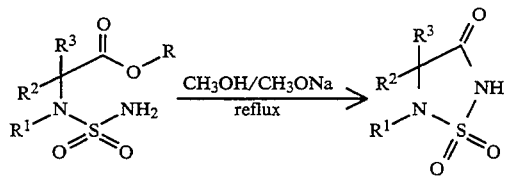

Examples of reactions as in steps 2 to 4 are described in the literature in G. W. Muller, G. E. DuBois, J. Org. Chem. 54, 4471 (1989).

1,1-dioxo-1,2,5-thiadiazolidin-3-one derivatives (derivatives of step 4) are furthermore accessible by the methods of for example H. K. Vorreither, E. Ziegler, Monatsh. Chem. 96, 216 (1965), of J. W. Timberlake, W. J. Ray Jr., E. D. Stevens, J. Org. Chem. 54, 5824 (1989), and of C. -H. Lee, J. D. Korp, H. Kohn, J. Org. Chem. 54, 3077 (1989).

Fused compounds of step 4 from cyclic amino acid derivatives are accessible as described by C. -H Lee and H. Kohn in J. Org. Chem. 55, 6098 (1990).

Step 5

Alkylation with haloacetic esters, preferably with methyl bromoacetate, gives the 2-N-alkylated five-membered ring systems.

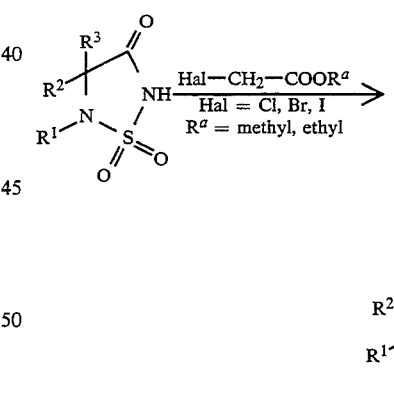

Step 6

Basic rearrangement of the acetic acid derivative gives the dihydrothiadiazine skeleton.

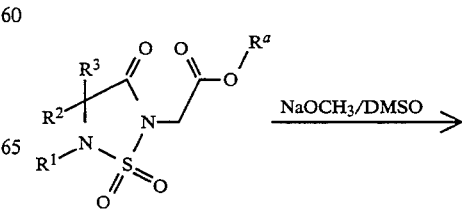

-continued

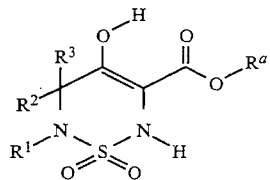

Step 7, (optional)

In the preparation of compounds of the general formula I in which R⁴ has a meaning other than a hydrogen atom, the compounds of the general formula R$^b$Hal in which R$^b$ denotes lower alkyl or aryl-lower-alkyl, are reacted to give the corresponding N-substituted alkyl derivatives.

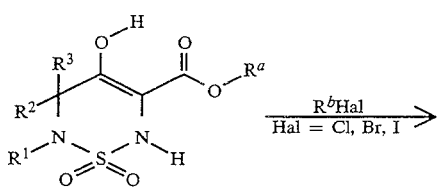

Step 8

When compounds of step 6 or 7 are reacted with amines in higher-boiling aromatic hydrocarbons, if appropriate with the use of generally customary amidation catalysts, R$^a$OH is eliminated and the compounds of the general formula I according to the invention are obtained.

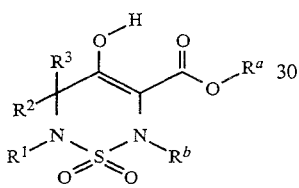

Steps 5 to 8 are similar to syntheses which have been published (J. G. Lombardino, E. H. Wiseman, W. M. McLamore, J. Med. Chem. 14, 1171 (1971), U.S. Pat. No. 3,591,584, DOS 1,943,265).

From step 5 on, the compounds according to the invention can alternatively be obtained by the following process variant:

Step 5, variant

If, in the above step 5, haloacetamides, which are readily obtainable from α-halocarboxylic acid halides and amines, are used instead of haloacetic esters, reaction with 1,1-dioxo-1,2,5-thiadiazolidin-3-ones gives the corresponding 2-(2-acetylamido)-1,1,-dioxo-1,2,5-thiadiazolidin-3-ones.

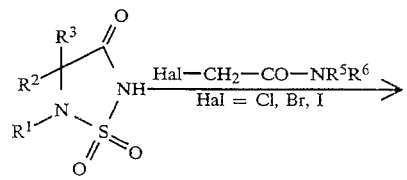

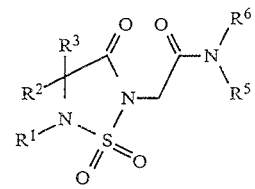

Step 6, variant

Here too, the basic rearrangement of reaction from the five-membered ring to the six-membered ring takes place as in the above step 6.

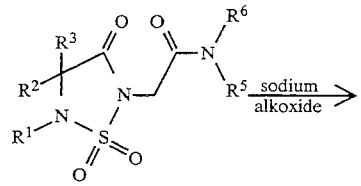

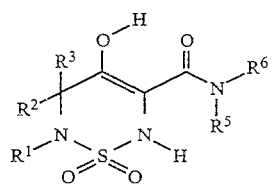

Step 7, variant (optional)

When preparing compounds of the general formula I in which R⁴ has a meaning other than a hydrogen atom, the reaction is carried out using compounds of the general formula R$^b$Hal, in which R$^b$ denotes lower alkyl or aryl-lower-alkyl, to give the corresponding N-substituted alkyl derivatives.

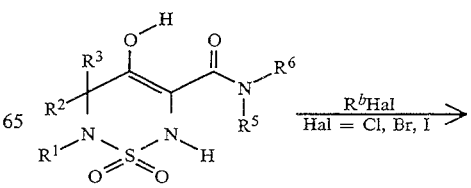

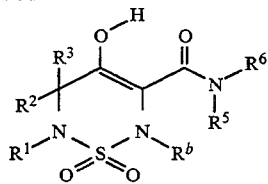

This reaction sequence has also been described (I. A. Perillo, C. B. Schapira, S. Lamdan, J. Heterocyclic Chem. 20, 155 (1983)).

Irrespective of whether enantiomerically pure or racemic amino acids are employed in step 1, both variants generally give racemic mixtures of the target compounds. These can be converted into the enantiomerically pure compounds by conventional processes (for example Wilen, Top. Stereochem. 6, 107 (1971), Wilen, Collet, Jacques, Tetrahedron 33, 2725 (1977), Boyl, Q. Rev. Chem. Soc. 25, 323 (1971)), for example by conversion into diastereomeric enol ethers, enol esters, acetals or ketals with optically pure alcohols, acids, aldehydes, ketones or reactive derivatives of these, followed by separation of the resulting diastereomers, for example by fractional crystallisation or by chromatographic methods, and finally by elimination of the chiral auxiliary groups or by conventional, chromatographic methods using chiral column materials.

If the amino acids used in step 1 have functional groups in $R^3$, these may have to be protected by generally customary methods (for example Houben-Weyl, Methoden der Organischen Chemie [Methods in Organic Chemistry], Volume 15, Georg Thieme Verlag, Stuttgart 1974; Th. W. Greene, Protective Groups in Organic Synthesis, John Wiley & Sons, New York 1981). The same applies to the radical $R^6$ when it contains a functional group and when such compounds of the general formula I are prepared by the above process variant.

The compounds of the general formula I according to the invention are novel substances.

Thiadiazinones are known from J. Chem. Res.(S), 1988, 94–95, furthermore from Chem. Abstr. 104, 207234 (1986) and from Chem. Abstr. 107, 89296 (1987) and Chem. Abstr. 106, 5093 (1987). Certain thiadiazines are known from J. Org. Chem. 29, 1905–1909 (1964), and furthermore from U.S. Pat. No. 2,956,997, U.S. Pat. No. 3,223,703 and U.S. Pat. No. 3,203,954. Certain benzothiazines, the so-called oxicams, are known from J. Med. Chem. 14, 1171–1175 (1971) and from J. Med. Chem. 16, 493–496 (1973). A pharmacological activity has been described for individual representatives from classes of the thiadiazinones and of the thiadiazines. The class of the oxicams embraces potent anti-inflammatory substances, for example piroxicam, which, however, have some disadvantages (Scrip 19, 984 (1985) or Drugs 35, 504 (1988)). Substances which are similar to the compounds according to the invention from the structural point of view have not been disclosed.

The compounds of the general formula I are valuable pharmaceutical active substances.

Surprisingly, the compounds according to the invention are distinguished by a powerful anti-inflammatory action and they are free from undesirable properties. Moreover, these compounds have powerful analgesic and antipyretic properties. It must be particularly emphasised that the compounds according to the invention are well tolerated and that ulcerogenic properties are absent. The compounds according to the invention are therefore suitable for the treatment of inflammatory and painful diseases in humans and animals. The clinical pictures which can be treated with the compounds according to the invention embrace all inflammatory conditions, such as, for example, inflammations of the skin such as radiodermatitis, psoriasis, acne, eczema, inflammations of the eye, such as, for example, conjunctivitis, inflammations in the ear, nose and throat region, such as, for example, catarrhal infections of the upper airways and sinusitis, inflammatory diseases of the vascular system, such as thrombophlebitis or vasculitis, and inflammations of the nervous system, such as, for example, neuralgias or inflammations of the nerves. Inflammatory diseases which are preferably to be treated are inflammations in the region of the locomotor system such as various types of arthritis, arthrosis, tendinitis, tendopathies, contusions and distortions, non-articular rheumatism syndrome, gout and lumbalgias. The compounds according to the invention are also particularly suitable for the treatment of certain diseases or disorders in which pain is in the fore. Mention should be made of post-operative pain conditions, pain following tooth extraction and migraine.

Tests for anti-inflammatory action (by the methods of C. A. Winter, E. A. Risley, G. W. Nuss; Proc. Soc. Exp. Biol. Med. 111, 544 (1962)) on groups with ten Wistar rats each have demonstrated that compounds according to the invention have a powerful anti-inflammatory activity. For example, the compound of Example 4 below shows an inhibition of 42% at a dosage rate of 200 mg/kg body weight (perorally).

Tests for analgesic properties (by the method of R. A. Turner, Screening Methods in Pharmacology, Academic Press, New York and London 1965, p. 113) have also demonstrated a powerful action of the compounds according to the invention. For example, the compound of Example 4 displayed a 100% protective effect at a dosage rate of 200 mg/kg of body weight (perorally).

The compounds according to the invention can be administered in a multiplicity of pharmaceutical formulations, such as, for example, tablets, coated tablets, capsules, liquid preparations to be taken orally, ointments, gels, plasters, solutions for injection or sprays, it being possible to use generally customary excipients and auxiliaries which are compatible with the compounds according to the invention.

The present invention also relates to pharmaceutical preparations (pharmaceuticals) which comprise, besides non-toxic, inert pharmaceutically acceptable excipients, one or more active substances according to the invention, or which are composed of one or more active substances according to the invention.

Non-toxic, inert pharmaceutically acceptable excipients are solid, semi-solid or liquid diluents, fillers and formulation auxiliaries of any type.

Preferred pharmaceutical preparations are tablets, coated tablets, capsules, granules, suppositories, solutions, suspensions and emulsions, pastes, ointments, gels, creams, lotions, powders, sprays and aerosols.

Tablets, coated tablets, capsules and granules can comprise the active substance, or active substances, besides the customary excipients. These include a) fillers and extenders, for example starches, lactose, sucrose, glucose, mannitol and silica, b) binders, for example carboxymethyl cellulose, alginates, gelatin, polyvinylpyrrolidone, c) humectants, for example glycerol, d)

disintegrants, for example agar-agar, calcium carbonate and sodium bicarbonate, e) solution retardants, for example paraffin, f) resorption accelerators, g) wetting agents, for example cetyl alcohol or glycerol monostearate, h) adsorbents, for example kaolin and bentonite, and i) gliding agents, for example talc, calcium stearate, magnesium stearate and solid polyethylene glycols, or mixtures of the substances listed under a) to i).

The tablets, coated tablets, capsules and granules can be provided with customary coatings, for example sugars, or coating lacquers which can optionally contain pacifying agents, and they can also be composed in such a manner that they release the active substance or active substances, only, or preferentially, in a certain part of the intestinal tract, if appropriate in a delayed manner, it being possible to use for example polymeric substances and waxes as embedding materials.

The active substance, or active substances, can also be in microencapsulated form, if appropriate together with one or more of the abovementioned excipients.

Suppositories can comprise, besides the active substance or active substances, the customary water-soluble or water-insoluble excipients, for example polyethylene glycols, fats, for example cocoa fat, and higher esters (for example $C_{14}$-alcohol with $C_{16}$-fatty acid, or mixtures of these substances).

Creams comprise, beside the active substance or active substances, mainly fatty alcohols, for example lauryl, cetyl or stearyl alcohol, fatty acids, for example palmitic or stearic acid, liquid to solid waxes, for example isopropyl myristate, wool waxes or beeswax and/or hydrocarbons, for example petroleum jelly (petrolatum) or paraffin oil, as oily base. Emulsifiers which are preferably used are those having mainly hydrophilic properties, for example non-ionic emulsifiers, such as fatty acid esters of polyalcohols, ethylene oxide adducts thereof, such as polyglycerol fatty acid esters or polyoxyethylene sorbitan fatty acid esters (various types of Tween) or ionic emulsifiers, such as alkali metal salts of fatty alcohol sulphates, for example sodium lauryl sulphate, sodium cetyl sulphate or sodium stearyl sulphate. The aqueous phase can be additioned with agents which prevent the cream from drying out, for example polyalcohols, such as glycerol, sorbitol, propylene glycol and/or polyethylene glycols.

Suitable excipients for ointments are, besides the active substance or active substances, mainly hydrocarbons, for example petroleum jelly or paraffin oil, which preferably comprise suitable fatty alcohols or esters thereof, for example cetyl alcohol or wool waxes, to improve the water-binding capacity. Emulsifiers are suitable lipophilic substances, such as sorbitan fatty acid esters. The aqueous phase can be additioned with humectants, such as, for example, glycerol or propylene glycol.

Sprays and powders can comprise, besides the active substance or active substances, the customary excipients, for example lactose, talc, silica, aluminium hydroxide, calcium silicate and pulverulent polyamide, or mixtures of these substances. Sprays can additionally comprise the customary propellants.

Solutions and emulsions can comprise, besides the active substance or active substances, the customary excipients, such as solvents, solubilisers and emulsifiers, for example water, ethanol, isopropanol, ethyl carbonate, benzyl alcohol, benzyl benzoate, propylene glycol, 1,3-butylene glycol, oils, in particular cotton seed oil, groundnut oil, corn oil, castor oil, cashew nut oil and sesame seed oil, glycerol, glycerol formal, polyethylene glycols and fatty acid esters of sorbitan, or mixtures of these substances.

Suspensions can comprise, besides the active substance or active substances, the customary excipients, such as liquid diluents, for example ethanol, propylene glycol, suspending agents, for example ethoxylated isostearyl alcohols, polyoxyethylene sorbitol esters and sorbitan esters, microcrystalline cellulose, aluminium metahydroxide, bentonite, agar-agar or tragacanth, or mixtures of these substances.

The abovementioned formulations can also comprise colorants, preservatives and additives which improve odour and flavour, for example peppermint oil and eucalyptus oil, and sweeteners, for example saccharin.

The abovementioned pharmaceutical preparations are to comprise the therapeutically active compounds in a concentration of approximately 0.1 to 99.5, preferably approximately 0.5 to 95% by weight of the total mixture.

The abovementioned pharmaceutical preparations may comprise, apart from the active substances according to the invention, further pharmaceutical active substances.

The abovementioned pharmaceutical preparations are prepared in a customary manner by known methods, for example by mixing the active substances with the excipients.

The present active substances or pharmaceutical preparations, which comprise one or more active substances can be used in human and veterinary medicine for the prevention, alleviation and/or curing of inflammatory diseases.

In general, it has proven as advantageous in human medicine to administer the active substance, or active substances, according to the invention in total doses of approximately 1 to approximately 1000 mg, preferably 10 to 500 mg, per unit dose when administering one to four unit doses per day to achieve the desired results.

However, it may be necessary to-deviate from the abovementioned dosage rates, specifically depending on the species and the body weight of the subject to be treated, the nature and severity of the disease, the type of preparation and administration of the pharmaceutical, and on the period or interval within which administration takes place. For example, in some cases it may suffice to manage with less than the abovementioned amount of active substance, while in other cases the abovementioned amount of active substance must be exceeded.

The examples which follow illustrate the invention in greater detail without restricting its scope thereto.

EXAMPLES

Example 1

5,6-Dihydro-4-hydroxy-2-methyl-1,1-dioxo-N-phenyl-2H-pyrrolidino[1,2-e][1,2,6]thiadiazine-3-carboxamide 128 mmol of methyl 5,6-dihydro-4-hydroxy-2-methyl-1,1-dioxo-2H-pyrrolidino[1,2-e][1,2,6]thiadiazine-3-carboxylate and 1.0 equivalent of freshly distilled aniline are introduced into 300 ml of dry xylene. At an oil-bath temperature of 150° to 160° C., the methanol freed in the reaction is additionally removed by passing in a gentle stream of nitrogen via a distillation bridge. If appropriate, deficient xylene in the reaction batch is replenished. The solid which precipitates in the batch after cooling is filtered off, washed with xylene and diisopropyl ether and recrystallised from a diisopropyl ether/acetone mixture. Alkaline extraction of the xylene solution, acidification of the aqueous solution and the re-extraction with ethyl acetate gives, after washing with sodium chloride solution, drying and stripping of the solvent, more crystalline crude product, which is also recrystallised. In this manner, the desired title compound in a yield of 50% (average).

M.p.: 163.5–164.5° C.

$^1$H NMR (CDCl$_3$): δ=1.75–2.64 (m, 4H, 5-CH$_2$ and 6-CH$_2$), 3.12 (s, 3H, CH3), 3.23–4.06 (m, 2H, 7-CH$_2$), 4.36 (t, J=8 Hz, 1H, 4a-CH), 7.03–7.69 (m, 5H, Ph-H), 8.10 (s-broad, 1H, NH), 13.05 (s-broad, 1H, OH).

IR (KBr): 3340, 3030–2890, 1645, 1595, 1535, 1490, 1445, 1365, 1325, 1300, 1235, 1185, 1150, 1080, 1050, 1030, 1000, 880, 865, 815, 770, 760, 700, 630 cm$^{-1}$.

MS: m/e=323 (M$^+ \cdot$), 231, 204, 162, 161, 134, 133, 120, 93 (100%), 84, 77, 70, 69.

| Elemental analysis: | % C | % H | % N | % S |
|---|---|---|---|---|
| (C$_{14}$H$_{17}$N$_3$O$_4$S) calculated: | 52.00 | 5.30 | 13.00 | 9.91 |
| found: | 51.91 | 5.19 | 12.89 | 10.01 |

Example 2

5,6-Dihydro-4-hydroxy-N-(2-methoxy-5-methylphenyl)-2-methyl-1,1-dioxo-2H-pyrrolidino[1,2-e][1,2,6]thiadiazine-3-carboxamide The synthesis is carried out analogously to Example 1 using 1.0 equivalent of 2-methoxy-5-methylaniline instead of aniline. After recrystallisation from ethyl acetate, the title compound is obtained in a yield of 69%.

M.p.: 163.5–164.5° C.

$^1$H NMR (CDCl$_3$): δ=1.66–2.63 (m, 4H, 5-CH$_2$ and 6-CH$_2$), 2.36 (s,3H, Ph-CH$_3$), 3.15 (s, 3H, N-CH$_3$), 3.25–4.03 (m, 2H, 7-CH$_2$), 3.91 (s, 3H, O-CH$_3$), 4.33 (t, J=8 Hz, 1H, 4a-CH), 6.61–7.00 (m, 2H, 2 Ar-H), 8.09 (s, 1H, 1Ar-H), 8.56 (s-broad, 1H, NH).

IR (KBr): 3350, 2940, 1635, 1595, 1540, 1485, 1450, 1440, 1365, 1345, 1315, 1290, 1250, 1225, 1215, 1185, 1170, 1135, 1080, 1025, 1000, 930, 920, 895, 875, 840, 810, 765, 720, 690, 630 cm$^{-1}$.

MS: m/e=367 (M$^+ \cdot$), 191, 175, 149, 138, 137, (100%), 122, 106.

Example 3

5,6-Dihydro-4-hydroxy-N-(2-methoxyphenyl)-2-methyl-1,1-dioxo-2H-pyrrolidino[1,2-e][1,2,6]thiadiazine-3-carboxamide The synthesis is effected analogously to Example 1 using 1.0 equivalent of o-anisidine instead of aniline. After recrystallisation from a diisopropyl ether/acetone mixture, the title compound is obtained in a yield of 80%.

M.p.: 161–162.5° C.

$^1$H NMR (d$_6$ DMSO): δ=1.59–2.64 (m, 4H, 5-CH$_2$ and 6-CH$_2$), 2.99–4.07 (m, 2H, 7-CH$_2$), 3.11 (s, 3H, N-CH$_3$), 3.87 (s, 3H, O-CH$_3$), 4.38 (t, J=7 Hz, 1H, 4a-CH), 6.81–7.37 (m, 3H, 3 Ar-H), 7.64–7.97 (m, 1H, 1Ar-H), 9.13 (s, 1H, NH).

IR (KBr): 3370, 2970, 1635, 1595, 1540, 1485, 1460, 1435, 1365, 1340, 1305, 1290, 1250, 1210, 1175, 1165, 1125, 1070, 1050, 1025, 995, 940, 915, 860, 850, 630 cm$^{-1}$.

Example 4

5,6-Dihydro-4-hydroxy-2-methyl-1,1-dioxo-N-(2-pyridyl)-2H-pyrrolidino[1,2-e][1,2,6]thiadiazine-3-carboxamide The synthesis is effected analogously to Example 1 using 1.0 equivalent of 2-aminopyridine instead of aniline. After recrystallisation from acetone, the title compound is obtained in a yield of 44%.

M.p.: 172.5–173° C.

$^1$H NMR (d$_6$ DMSO): δ=1.66–2.43 (m, 4H, 5-CH$_2$, 6-CH$_2$), 2.76 and 3.06 (2s, 3H, CH$_3$), 3.17–3.86 (m, 2H, 7-CH$_2$), 4.35 (t, J=7 Hz, 1H, 4a-CH), 4.87 (s, 1H, 3-CH), 7.00–7.35 (m, 1H, 1Ar-H), 7.66–8.12 (m, 2H, 2Ar-H), 8.21–8.46 (m, 1H, 1Ar-H), 10.69 (S-broad, 1H, NH), keto:enol=1:5.

IR (KBr): 3440, 3160, 2980, 2880, 1640, 1590, 1575, 1535, 1510, 1435, 1365, 1340, 1330, 1305, 1285, 1235, 1210, 1170, 1140, 1065, 1030, 995, 930, 890, 815, 775, 740, 635, 625 cm$^{-1}$.

MS: m/e=324 (M$^+ \cdot$), 260, 204, 191, 164, 163, 148, 138, 134, 123, 122, 121, 94 (100%), 78, 70, 69, 68, 67, 55.

Example 5

5,6-Dihydro-4-hydroxy-2-methyl-N-(5-methyl-3-isoxazolyl)-1,1-dioxo-2H-pyrrolidino[1,2-e][1,2,6]thiadiazine-3-carboxamide The synthesis is effected analogously to Example 1 using 1.0 equivalent of 3-amino-5-methylisoxazole instead of aniline. After recrystallisation from ethyl acetate, the title compound is obtained in a yield of 48%.

M.p.: 194° C.; with decomposition $^1$H NMR (d$_6$ DMSO): δ=1.71–2.48 (m, 4H, 5-CH$_2$, 6-CH$_2$), 2.40 (s,3H, Ar-CH$_3$), 2.74 and 3.00 (2s, 3H, N-CH$_3$), 3.31–3.92 (m, 2H, 7-CH$_2$), 4.40 (t, J=7 Hz, 1H, 4a-CH), 4.69 (s, 1H, 3-CH), 6.56 (s, 1H, Ar-H), 10.84 (s, 1H, NH), keto:enol-1:6.

IR (KBr): 3420, 3190, 3060, 2990, 2960, 2930, 2890, 1635, 1610, 1530, 1470, 1440, 1370, 1340, 1320, 1270, 1245, 1210, 1185, 1165, 1150, 1075, 1055, 1030, 1010, 995, 925, 915, 875, 800, 755, 750, 630 cm$^{-1}$.

MS: m/e=328 (M$^+ \cdot$), 204, 195, 180, 167, 162, 152, 139, 126, 125, 124, 98, 84, 83, 82, 70 (100%), 69, 68, 55.

Example 6

5,6-Dihydro-4-hydroxy-2-methyl-1,1-dioxo-N-(2-thiazolyl)-2H-pyrrolidino[1,2-e][1,2,6]thiadiazine-3-carboxamide The synthesis is effected analogously to Example 1 using 1.0 equivalent of 2-aminothiazole instead of aniline. After purification by column chromatography over silica gel using an eluent mixture of diisopropyl ether/ethyl acetate/formic acid=150/50/1, the title compound is obtained in a yield of 44%.

M.p.: 166°–168.5° C.

$^1$H NMR (d$_6$ DMSO): δ=1.56–2.61 (m, 4H, 5-CH$_2$, 6-CH$_2$), 2.74 and 3.05 (2s, 3H, N-CH$_3$), 3.05–3.87 (m, 2H, 7-CH$_2$), 4.33 (t, J=7 Hz, 1H, 4a-CH), 4.79 (s, 1H, 3-CH), 7.18 (d, J=4 Hz, 1H, 1 Ar-H), 7.56 (d, J =4 Hz, 1H, 1 Ar-H), keto:enol=1:12.

IR (KBr): 3100, 2970, 1630, 1530, 1485, 1440, 1425, 1365, 1340, 1325, 1270, 1240, 1210, 1190, 1165, 1145, 1060, 1030, 990, 945, 930, 915, 895, 825, 785, 760, 720, 680, 670, 625 cm$^{-1}$.

Example 7

N-benzyl-5,6-dihydro-4-hydroxy-2-methyl-1,1-dioxo-2H-pyrrolidino[1,2-e][1,2,6]thiadiazine-3-carboxamide The synthesis is effected analogously to Example 1 using 1.0 equivalent of benzylamine instead of aniline. After washing the crystalline crude product with a mixture of diisopropyl ether/tert.-butyl methyl ether, the title compound is obtained in a yield of 11%.

M.p.: 123–126° C.

$^1$H NMR (d$_6$ DMSO): δ=1.59–2.36 (m, 4H, 5-CH$_2$, 6-CH$_2$), 2.89–3.92 (m, 2H, 7-CH$_2$), 2.97 (s, 3H, N-CH$_3$), 4.13–4.56 (m, 3H, CH$_2$-Ph and 4a-CH), 7.30 (s, 5H, Ph-H), 8.86 (t-broad, J=7 Hz, 1H, NH).

IR (KBr): 3330, 3030, 2970, 2920, 1635, 1535, 1495, 1450, 1365, 1335, 1235, 1200, 1170, 1145, 1095, 1070, 1025, 995, 985, 915, 865, 825, 765, 740, 700, 690, 665, 620 cm$^{-1}$.

The compound methyl 5,6-dihydro-4-hydroxy-2-methyl- 1,1-dioxo-2H-pyrrolidono[1,2-e][1,2,6]thiadiazine-3-carboxylate, which has been used as starting material in Examples 1 to 7, was prepared as described in steps A to G below:

Step A

Methyl pyrrolidine-2-carboxylate hydrochloride 600 ml of technical-grade methanol are introduced into a multinecked flask equipped with dropping funnel and internal thermometer, with ice/sodium chloride cooling. 2.4 mol of thionyl chloride are added dropwise in such a way that the temperature of the reaction solution does not exceed −5° C. Then, 2.18 mol of proline are added in portions in the course of approximately 10 minutes. The mixture is stirred for approximately 4 hours at 40° C. and subsequently for three days at room temperature, and the solution is greatly concentrated, the residue is taken up several times in methanol to remove excess thionyl chloride, and the mixture is reconcentrated. After drying the product for several hours in a lukewarm water bath in an evacuated flask, the target compound is obtained in quantitative yield. Some of the oily crude product crystallises after being left to stand over several days.

1H NMR (d$_4$ methanol): δ=1.81–2.69 (m, 4H, 3-CH$_2$, 4-CH$_2$), 3.23–3.59 (m. 2H, 5-CH$_2$), 3.84 (s, 3H, CH$_3$), 4.46 (t, J=7 Hz, 1H, 2-CH), 4.81 (s, 2H, NH, HCl)

IR (oil film): 3390 (broad), 2959 (broad), 2740, 1745, 1570, 1445, 1245, 1050, 1000, 920 cm$^{-1}$.

Step B

Methyl N-[N-benzyloxycarbonyl)sulphamoyl]pyrrolidine-2-carboxylate 275 mmol of chlorosulphonyl isocyanate in 300 ml of dry methylene chloride are introduced at −30° C. into a 3-necked flask equipped with dropping funnel and internal thermometer. 275 mmol of benzyl alcohol are added dropwise in such a way that the temperature of the reaction solution does not exceed 5° C. The mixture is subsequently stirred for one and a half hours at 0° C., and a suspension of 302 mmol of methyl pyrrolidine-2-carboxylate hydrochloride and 815 mmol of triethylamine in 1 l of dry methylene chloride is then also added dropwise in such a way that the batch does not exceed 5° C. The reaction solution is stirred overnight and then extracted several times at room temperature with a total of 350 ml of 2N hydrochloric acid, and the extract is washed with sodium chloride solution, dried and evaporated on a rotary evaporator. The title compound is obtained in a yield of approximately 90% in the form of an oil.

$^1$H NMR (CDCl$_3$): δ=1.66–2.40 (m, 4H, 3-CH$_2$, 4-CH$_2$), 3.31–3.86 (m, 2H, 5-CH$_2$), 3.71 (s, 3H, CH$_3$), 4.64 (dd, J$_1$=7 Hz, J$_2$=3 Hz, 1H, 2-CH), 5.17 (s, 2H, CH$_2$-Ph), 7.35 (s, 5H, Ph-H), 7.84 (s-broad, 1H, NH).

IR (oil film): 2960 (broad), 1740, 1650, 1600, 1450, 1360, 1340, 1285, 1215, 1155, 1100, 1080, 1040, 1025, 845, 750, 700 cm$^{-1}$.

Step C

Methyl N-sulphamoylpyrrolidine-2-carboxylate 228 mmol of methyl N-[N'-(benzyloxycarbonyl)sulphamoyl]pyrrolidine-carboxylate are hydrogenated in 200 ml of methanol at room temperature over palladium/active charcoal. The target compound precipitates in the reaction vessel during the hydrogenation. The catalyst containing precipitate is filtered off with suction and boiled several times with acetone, during which process the product dissolves. After the mixture has been filtered while hot and the solvent has been stripped off, the title compound is obtained in 76% (average) yield as a crystalline crude product, which is washed using ethyl acetate.

M.p.: 166–167.5° C.

$^1$H-NMR (d$_6$ DMSO): δ=1.61–2.30 (m, 4H, 3-CH$_2$, 4-CH$_2$), 3.26 (t, J=6 Hz, 2H, 5-CH$_2$), 3.61, (s, 3H, CH$_3$), 4.17 (dd, J$_1$=8 Hz, J$_2$=3 Hz, 1H, 5-CH) 6.81 (s, 2H, NH$_2$).

IR (KBr): 3340, 3240, 3100, 2980, 2955, 2870, 2675, 2495, 1735, 1655, 1560, 1460, 1440, 1385, 1360, 1325, 1280, 1220, 1200, 1185, 1165, 1150, 1135, 1100, 1070, 1015, 990, 910, 830, 760 cm$^{-1}$.

Step D 1,1-Dioxo-pyrrolidino[4,5-d][1,2,5]thiadiazolidin-3-one 377 mmol of methyl N-sulphamoylpyrrolidine-2-carboxylate are refluxed for three hours in a freshly prepared solution of 1.4 equivalents of sodium methanolate in methanol. Stripping off the solvent, taking up the residue in 0.3 l of ethyl acetate, extracting the organic solution several times using 2 N hydrochloric acid, washing the extract with sodium chloride solution, drying it and stripping off the solvent gives the colourless, crystalline title compound in a yield of approximately 40%.

M.p.: 134–135° C.

$^1$H NMR (d$_6$-DMSO): δ=1.48–2.41 (m, 4H, 4-CH$_2$, 5-CH$_2$), 3.00–3.83 (m, 2H, 6-CH$_2$), 4.56 (dd, J$_1$=7 Hz, J$_2$=1 Hz, 1H, 3a-CH), 9.58 (s-broad, 1H, NH).

IR (KBr): 3130 (broad), 2670, 1635, 1615, 1460, 1365, 1335, 1300, 1265, 1180, 1090, 1070, 990, 975, 965, 930, 925, 885, 700 cm$^{-1}$.

MS: m/e=176 (M$^{+\cdot}$), 148, 133, 106, 79, 69, (100 %), 68, 64, 48.

| Elemental analysis: | | % C | % H | % N | % S |
|---|---|---|---|---|---|
| (C$_5$H$_8$N$_2$O$_3$S) | calculated: | 34.08 | 4.58 | 15.90 | 18.20 |
| | found: | 34.47 | 4.57 | 15.42 | 17.55 |

Step E

Methyl 2-(1',1'-dioxo-pyrrolidino[4,5-d][1,2,5]thiadiazo-lidin-3'-on-2'-yl)acetate 329 mmol of 1,1-dioxo-pyrrolidino[4,5d]-[1,2,5]thiadiazolidin-3-one are dissolved in 400 ml of dry THF and refluxed with 427 mmol of triethylamine and 395 mmol of methyl bromoacetate for three hours. The ammonium salt is filtered off with suction and washed, the organic solution is evaporated to a large extent on a rotary evaporator, the residue is taken up in ethyl acetate and extracted several times, first with 2 N hydrochloric acid and then with sodium chloride solution, dried and evaporated on a rotary evaporator. Most of the crude product, which starts as an oil, crystallises out when left to stand. The oily mother liquor which remains is chromatographed over silica gel using diisopropyl ether/ethyl acetate/formic acid=100/50/1. Washing of the combined crystals with tert.-butyl methyl ether gives the title compound in a yield of 79% (average).

m.p.: 63–63.5° C.

$^1$H NMR (CDCl$_3$): $\delta=1.69$–2.61 (m, 4H, 4'-CH$_2$, 5'-CH$_2$), 3.12–4.08 (m, 2H, 6'-CH$_2$), 3.79 (s, 3H, CH$_3$), 4.25 (d, J=2 Hz, 2H, 2-CH$_2$), 4.53 (dd, J$_1$=7 Hz, J$_2$=3 Hz, 1H, 3a-CH).

IR (KBr): 3490, 3460, 2980, 2960, 2880, 1750, 1445, 1410, 1380, 1360, 1320, 1305, 1295, 1250, 1200, 1110, 1065, 1040, 990, 970, 950, 925, 905, 885, 870, 815, 760, 715, 660, 630 cm$^{-1}$

Step F

Methyl 5,6-dihydro-4-hydroxy-1,1-dioxo-2H-pyrrolidino[1,2-e][1,2,6]-thiadiazine-3-carboxylate 332 mmol of sodium are dissolved in 200 ml of absolute methanol. The sodium methanolate obtained after the solvent has been stripped off is suspended in dry DMSO, and the suspension is cooled in an ice-bath. A solution, also pre-cooled, of 166 mmol of methyl 2-(1'1'-dioxopyrrolidino[4,5-d][1,2,5]thiadiazolidin-3'on-2'-yl) acetate in DMSO is rapidly added dropwise. When the addition has ended, stirring is continued for 15 minutes, and 200 ml of hydrochloric acid/ice mixture are then added. The mixture is then extracted using ethyl acetate, and the ethyl acetate phase is extracted several times using 2N sodium hydroxide solution. Acidification of the aqueous alkaline solution with 2N hydrochloric acid, re-extraction with ethyl acetate, washing of the organic solution using sodium chloride solution, drying and stripping off the solvent gives an oily crude product which crystallises when treated with tert.-butyl methyl ether. This gives the pure title compound in a yield of 20 to 30% (average).

M.p.: 109.5–110° C.

$^1$H NMR (CDCl$_3$): $\delta=1.73$–2.53 (m, 4H, 5-CH$_2$, 6-CH$_2$), 2.91–4.66 (m, 2H, 7-CH$_2$), 3.83 (s, 3H, CH$_3$), 4.54 (t, J=5 Hz, 1H, 4a-CH), 5.91 (s-broad, 1H, NH), 11.15 (s, 1H, OH).

IR (KBr): 3280, 2950, 2890, 1670, 1620, 1450, 1410, 1380, 1310, 1250, 1225, 1175, 1155, 1110, 1090, 1060, 1040, 985, 895, 780 CM$^{-1}$.

MS: m/e=248 (M$^+$·), 216, 148, 124, 99, 87, 70, (100%), 68, 55.

Step G

Methyl 5,6-dihydro-4-hydroxy-2-methyl-1,1-dioxo-2H-pyrrolidino[1,2-e][1,2,6]thiadiazine-3-carboxylate 2.5 equivalents of a 2.5-molar solution of butyllithium in hexane are added dropwise at $-30°$ C. to a solution of 86 mmol of methyl 5,6-dihydro-4-hydroxy-1,1-dioxo-2H-pyrrolidino[1,2-e][1,2,6]thiadiazine-3-carboxylate in 350 ml of dry THF in such a manner that the reaction temperature does not exceed $-25°$ C. When the addition has ended, the mixture is stirred for 20 minutes at low temperature, and 3.0 equivalents of methyl iodide in dry THF are subsequently added dropwise, also at $-30°$ C. After the batch has been stirred for 20 minutes at low temperature, it is allowed to warm to room temperature, and stirring is continued for a further 15 hours. Rendering the mixture weakly acidic by adding dilute hydrochloric acid, stripping off most of the solvent in vacuo, taking up the residue in ethyl acetate, washing of the ethyl acetate solution with sodium chloride solution, drying and finally stripping off the solvent yields a reddish-brown, oily crude product which is chromatographed over silica gel using a solvent mixture of diisopropyl ether/ethyl acetate/formic acid=100/50/1. After tert.-butyl methyl ether has been added, the oily product fraction crystallises to give the pale yellow title compound in an average yield of 46%.

M.p. 89.5–90.5° C.

$^1$H NMR (CDCl$_3$): $\delta=1.73$–2.58 (m, 4H, 5-CH$_2$), 3.10 (s, 3H, N-CH$_3$), 3.20–3.96 (m, 2H, 7-CH$_2$), 3.86 (s, 3H, O-CH$_3$), 4.35 (t, J=7 Hz, 1H, 4a-CH), 11.83 (s, 1H, OH).

IR (KBr): 2980, 2950, 1665, 1605, 1440, 1365, 1335, 1245, 1210, 1155, 1060, 1035, 995, 965, 855, 820, 805, 780, 765, 700, 680 cm$^{-1}$.

Example 8

2-Ethyl-5,6-dihydro-4-hydroxy-1,1-dioxo-N-phenyl-2H-pyrrolidino[1,2-e][1,2,6]thiadiazine-3-carboxamide The synthesis is effected analogously to Example 1 using in each case 1.0 equivalent of methyl 2-ethyl-5,6-dihydro-4-hydroxy-1,1-dioxo-2H-pyrrolidino[1,2-e][1,2,6]thiadiazine-3-carboxylate and aniline. Recrystallisation from a diisopropyl ether/acetone mixture gives the title compound in a yield of 35%.

M.p.: 132–133° C.

$^1$H NMR (CDCl$_3$): $\delta=1.31$ (t,J=7 Hz, 3H, CH$_3$) 1.66–2.58 (m, 4H, 5-CH$_2$ and 6-CH$_2$) 3.13–3.97 (m, 4H, 7-CH$_2$ and N-CH$_2$), 4.28 (dd, J$_1$=7 Hz, J$_2$=12 Hz, 1H, 4a-CH), 7.00–7.73 (m, 5H, Ph-H), 8.08 (s-broad, 1H, NH).

IR (KBr): 3300, 2970, 2870, 1630, 1595, 1535, 1495, 1445, 1325, 1230, 1165, 1090, 1060, 1040, 1030, 990, 955, 930, 900, 890, 855, 795, 745, 685 cm$^{-1}$.

MS: m/e=337 (M$^+$·), 218, 161, 147, 120, 93 (100%), 92, 77, 70, 69, 68, 56.

The compound methyl 2-ethyl-5,6-dihydro-4-hydroxy-1,1-dioxo-2H-pyrrolidino[1,2e][1,2,6]thiadiazine-3-carboxylate, which is used as starting material in Example 8, was obtained analogously to steps A to G using ethyl iodide instead of methyl iodide in Step G.

Example 9

2-Benzyl-5,6-dihydro-4-hydroxy-1,1-dioxo-N-phenyl-2H-pyrrolidino[1,2-e][1,2,6]thiadiazine-3-carboxamide The synthesis is effected analogously to Example 1 using in each case 1.0 equivalent of methyl 2-benzyl-5,6-dihydro-4-hydroxy-1,1-dioxo-2H-pyrrolidino-[1,2-e][1,2,6]thiadiazine-3-carboxylate and aniline. Recrystallisation from a diisopropyl ether/acetone mixture gives the title compound in a yield of 21%.

M.p.: 147–149° C.

$^1$H NMR (CDCl$_3$): $\delta=1.66$–2.56 (m, 4H, 5-CH$_2$ and 6-CH$_2$), 3.20–3.91 (m, 2H, 7-CH$_2$), 3.97–4.28 (m, 1H, 4a-CH), 4.59 (s-broad, 2H, CH$_2$-Ph), 6.87–7.64 (m, 11H, 2×5 Ph-H and 1NH).

IR (KBr): 3360, 3310, 2920, 2860, 1635, 1595, 1535, 1490, 1445, 1420, 1405, 1330, 1315, 1230, 1215, 1160, 1035, 1025, 975, 920, 890, 850, 805, 790 cm$^{-1}$.

MS: m/e=399 (M$^+$·), 308, 280, 238, 147, 120, 93, 92, 91, 77, 70 (100 %), 69, 68, 65.

The compound methyl 2-benzyl-5,6-dihydro-4-hydroxy-1,1-dioxo-2H-pyrrolidino[1,2-e][1,2,6]-thiadiazine-3-carboxylate, which is used as starting material in Example 9, was obtained analogously to Steps A to G using benzyl bromide instead of methyl iodide in Step G.

Example 10

5,6-Dihydro-4-hydroxy-2-methyl-1,1-dioxo-N-phenyl-2H-piperidino[1,2-e][1,2,6]thiadiazine-3-carboxamide The synthesis is effected analogously to Example 1 using in each case 1 equivalent of methyl 5,6-dihydro-4-hydroxy-2-methyl-1,1-dioxo-2H-piperidino[1,2-e][1,2,6]-thiadiazine-3-carboxylate and aniline. Purification over silica gel by column chromatography gives the title compound in a yield of 50%.

M.p.: 214–215° C., with decomposition $^1$H NMR (d$_6$ DMSO): δ=1.22–3.00 (m, 8H, 5-CH$_2$, 6-CH$_2$, 7-CH$_2$ and 8-CH$_2$), 2.90 (s, 3H, N-CH$_3$), 3.44–3.80 (m, 1H, 4a-CH), 6.96–7.76 (m, 5H, Ph-H), 9.92 (s, 1H, NH), 13.76 (s-broad, 1H, OH), IR (KBr): 3330, 2990, 2950, 2920, 2850, 1635, 1595, 1530, 1500, 1445, 1355, 1340, 1325, 1295, 1260, 1225, 1210, 1180, 1170, 1140, 1105, 1080, 1065, 1050, 1035, 1005, 995, 955, 940, 925, 905, 895, 875, 820, 805, 770, 750, 740, 700, 635 cm$^{-1}$.

MS: m/e=337 (M$^+$·), 176, 161, 134, 133, 120, 93 (100%), 92, 84, 83, 77, 66, 65, 56, 55.

| Elemental analysis: | | % C | % H | % N | % S |
|---|---|---|---|---|---|
| (C$_{15}$H$_{19}$N$_3$O$_4$S) | calculated: | 53.38 | 5.67 | 12.46 | 9.50 |
| | found: | 53.52 | 5.21 | 12.40 | 9.50 |

The compound methyl 5,6-dihydro-4-hydroxy-2-methyl-1,1-dioxo-2H-piperidino[1,2-e][1,2,6]thiadiazine-3-carboxylate, which is as starting material in Example 10, was obtained analogously to Steps A to G using piperidine-2-carboxylic acid instead of proline in Step A.

Example 11

6-Benzyl-5,6-dihydro-4-hydroxy-2-methyl-1,1-dioxo-N-phenyl-2H-1,2,6-thiadiazine-3-carboxamide The synthesis is effected analogously to Example 1 using in each case 1 equivalent of methyl 6-benzyl-5,6-dihydro-4-hydroxy-2-methyl-1,1-dioxo-2H-1,2,6-thiadiazine-3-carboxylate and aniline. Recrystallisation from a diisopropyl ether/acetone mixture gives the title compound in a yield of 54%.

M.p.: 197–198° C.

$^1$H NMR (d$_6$ DMSO): δ=2.96 (s, 3H, CH$_3$), 3.79 (s, 2H, 5-CH$_2$), 4.33 (s, 2H, Ph-CH$_2$), 7.00–7.79 (m, 10H, 2×5 Ph-H), 9.89 (s, 1H, NH)

IR (KBr): 3350, 1640, 1595, 1540, 1490, 1445, 1430, 1395, 1345, 1330, 1290, 1250, 1205, 1165, 1145, 1120, 1090, 1065, 1040, 1110, 975, 935, 910, 885, 845, 825, 815, 770, 760, 730, 700, 660, 640 cm$^{-1}$.

MS: m/e=373 (M$^+$·), 254, 190, 173, 161, 147, 133, 120, 106, 93 (100 %), 77, 69, 65.

| Elemental analysis: | | % C | % H | % N | % S |
|---|---|---|---|---|---|
| (C$_{18}$H$_{19}$N$_3$O$_4$S) | calculated: | 57.90 | 5.13 | 11.25 | 8.59 |
| | found: | 57.89 | 5.26 | 11.18 | 8.45 |

Example 12

6-Benzyl-5,6-dihydro-4-hydroxy-2-methyl-N-(5-methyl-3-isoxazolyl)-1,1-dioxo-2H- 1,2,6-thiadiazine-3-carboxamide The synthesis is effected analogously to Example 1 using in each case 1 equivalent of methyl 6-benzyl-5,6-dihydro-4-hydroxy-2-methyl-1,1-dioxo-2H-1,2,6-thiadiazine-3-carboxylate and 3-amino-5-methylisoxazole. Chromatography over silica gel using a mixture of diisopropyl ether/formic acid=100/1 or recrystallisation from a diisopropyl ether/acetone mixture gives the title compound in a yield of 59%.

M.p.: 199–199.5° C.

$^1$H NMR (d$_6$ DMSO): δ=2.38 (s, 3H, Ar-CH$_3$), 2.92 (s, 3H, N-CH$_3$), 3.81 (S, 2H, 5-CH$_2$), 4.33 (s, 2H, Ph-CH$_2$), 6.59 (s, 1H, Ar-H), 7.40 (s, 5H, Ph-H), 10.83 (s, 1H, NH).

IR (KBr): 3200, 1650, 1610, 1545, 1535, 1470, 1450, 1435, 1380, 1355, 1330, 1275, 1250, 1220, 1170, 1165, 1125, 1085, 1055, 1030, 1010, 990, 955, 935, 935, 900, 885, 860, 830, 810, 785, 755, 735, 695, 655, 620 cm$^{-1}$.

| Elemental analysis: | | % C | % H | % N | % S |
|---|---|---|---|---|---|
| (C$_{16}$H$_{18}$N$_4$O$_5$S) | calculated: | 50.79 | 4.79 | 14.81 | 8.47 |
| | found: | 50.66 | 4.67 | 14.71 | 8.56 |

The compound methyl 6-benzyl-5,6-dihydro-4-hydroxy-2-methyl-1,1-dioxo-2H-1,2,6-thiadiazine-3-carboxylate, which is used as starting material in Examples 11 and 12, was obtained analogously to Steps A to G using N-benzylglycine instead of proline in Step A.

Example 13

5,6-Dihydro-4-hydroxy-2,6-dimethyl-N-(2-pyridyl)-1,1-dioxo-2H-1,2,6-thiadiazine-3-carboxamide The synthesis was effected analogously to Example 1 using in each case 1.0 equivalent of methyl 5,6-dihydro-4-hydroxy-2,6-dimethyl-1,1-dioxo-2H-1,2,6-thiadiazine-3-carboxylate and 2-aminopyridine. Recrystallisation from a diisopropyl ether/tetrahydrofuran mixture gives the title compound in a yield of 55%.

M.p.: 185° C., with decomposition $^1$H NMR (d$_6$ DMSO): δ=2.73 (s, 3H, 2-N-CH$_3$), 2.92 (s, 3H, 6-N-CH$_3$) 3.86 (s, 2H, 5-CH$_2$), 7.08–7.35 (m, 1H, 1 At-H), 7.68–8.07 (m, 2H, 2 Ar-H), 8.26–8.46 (m, 1H, 1 Ar-H), 10.83 (s-broad, 1H, NH).

IR (KBr): 3360, 2940, 1660, 1605, 1590, 1575, 1525, 1460, 1430, 1380, 1350, 1345, 1325, 1300, 1240, 1210, 1175, 1160, 1125, 1115, 1050, 1010, 985, 970, 895, 885, 845, 830, 820, 790, 760, 730, 680, 630, 620, 610 cm$^{-1}$.

MS: m/e=298 (M$^+$·), 219, 203, 191, 163, 148, 134, 121, 94 (100%), 78, 67, 51.

Example 14

5,6-Dihydro-4-hydroxy-2,6-dimethyl-N-(5-methyl-3-isoxazolyl)-1,1-dioxo-2H-1,2,6-thiadiazine-3-carboxamide The synthesis was effected analogously to Example 1 using in each case 1.0 equivalent of methyl 5,6-dihydro-4-hydroxy-2,6-dimethyl-1,1-dioxo-2H-1,2,6-thiadiazine-3-carboxylate and 3-amino-5-methylisoxazole. Recrystallisation from a diisopropyl ether/tetrahydrofuran mixture gives the title compound in a yield of 49%.

M.p.: 189–191.5° C., with decomposition

¹H NMR (d₆ DMSO): δ=2.41 (s, 3H, Ar-CH₃), 2.73 (s, 3H, 2-N-CH₃), 2.89 (s, 3H, 6-N-CH₃), 3.94 (s, 2H, 5-CH₂), 6.59 (s, 1H, Ar-H), 10.83 (s, 1H, NH).

IR (KBr): 3195, 2930, 1645, 1610, 1535, 1470, 1445, 1435, 1400, 1375, 1355, 1340, 1330, 1300, 1275, 1255, 1220, 1200, 1170, 1145, 1125, 1115, 1060, 1030, 1005, 990, 975, 935, 885, 835, 785, 770, 760, 730, 630, 620 cm⁻¹.

MS: m/e=302 (M⁺·), 207, 195, 180, 167, 152 (100%), 138, 125, 111, 98, 83, 69, 57, 55.

The compound methyl 5,6-dihydro-4-hydroxy-2,6-dimethyl-1,1-dioxo-2H-1,2,6-thiadiazine-3-carboxylate, which is as starting material in Examples 13 and 14, was obtained analogously to Steps A to G using sarcosine instead of proline in Step A.

Example 15

If the procedure analogously to Example 1 is followed using the educts below of the general formulae II and III, the respective compounds I according to the invention of the table below are obtained (Examples 15a–15l):

| Educt Formula II | Educt Formula III | Product Formula I | Example; M.p. |
|---|---|---|---|
| (pyrrolidine-thiadiazine hydroxy enol methyl ester) | 4-methoxyaniline | corresponding anilide with 4-OCH₃ | 15a; 189–190° C. |
| " | 2-amino-1,4-dimethoxybenzene | corresponding 2,5-dimethoxyanilide | 15b; 153–154° C. |
| " | 4-chloroaniline | corresponding 4-chloroanilide | 15c; 188–189° C. |
| " | 2-amino-5-methylpyridine | corresponding 5-methylpyridin-2-yl amide | 15d; 162–163° C. |
| " | 2-amino-5-chloropyridine | corresponding 5-chloropyridin-2-yl amide | 15e; 155–156° C. |
| " | 2-amino-5-nitropyridine | corresponding 5-nitropyridin-2-yl amide | 15f; 202–204° C. |

| Educt Formula II | Educt Formula III | Product Formula I | Example; M.p. |
|---|---|---|---|
| (structure) | (structure) | (structure) | 15g; 190° C. (decomp.) |
| " | (structure) | (structure) | 15h; 131–132° C. |
| (structure) | (structure) | (structure) | 15i; 216–217° C. |
| (structure) | (structure) | (structure) | 15j; 198–199° C. |
| " | (structure) | (structure) | 15k; 210–211° C. |
| (structure) | (structure) | (structure) | 15l; 173–174° C. |

Example 16

Recipe for the preparation of tablets 1000 tablets are prepared from the compounds below in the manner described below. Thus, one tablet comprises, as active substance, 100 mg of 5,6-dihydro-4-hydroxy-2-methyl-1,1-dioxo-N-(2-pyridyl)-2H-pyrrolidino[1,2-e][1,2,6]thiadiazine-3-carboxamide.

| 1. 5,6-Dihydro-4-hydroxy-2-methyl-1,1-dioxo-N-(2-pyridyl)-2H-pyrrolidino-[1,2-e][1,2,6]-thiadiazine-3-carboxamide | 100 g |
|---|---|
| 2. Lactose | 263 g |
| 3. Microcrystalline cellulose | 120 g |
| 4. Maize starch | 60 g |
| 5. Magnesium stearate | 7 g |

1) and 2) are mixed, 3) and 4) are admixed, 5) is then added, and this is mixed and compressed directly.

Example 17

Recipe for the preparation of a cream:

The following recipe gives a 5% 5,6-dihydro-4-hydroxy-2-methyl-1,1-dioxo-N-(2-pyridyl)-2H-pyrrolidino-1,2-e][1,2,6]-thiadiazine-3-carboxamide cream (substances given in % by weight):

| | |
|---|---|
| 5,6-Dihydro-4-hydroxy-2-methyl-1,1-dioxo-N-(2-pyridyl)-2H-pyrrolidino[1,2-e][1,2,6]-thiadiazine-3-carboxamide | 5.00 |
| Emulsifier (mixture of sodium glycerol monostearate, sodium stearyl sulphate and sodium cetyl sulphate) | 10.00 |
| Triglycerides of medium chain length | 6.25 |
| Myristyl alcohol | 5.00 |
| POE-12 cetyl stearyl alcohol | 3.00 |
| Preservative | q.s. |
| Water | to 100.00 |

We claim:

1. Compounds of the general formula I

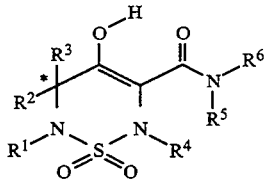

wherein $R^1$ is a lower alkyl group, an aryl group, a heteroaryl group or an aryl-lower-alkyl group, $R^2$ is a hydrogen atom, a lower alkyl group or an aryl group, $R^3$ is a hydrogen atom, a lower alkyl group, an aryl group, a heteroaryl group, an aryl-lower-alkyl group or a saturated, unbranched $C_1$-$C_4$, -alkyl group which is monosubstituted by a group selected from the group consisting of —$OR^7$, —$NR^8R^9$, —CO—$OR^{10}$, —$SR^{11}$, —CO—$NR^{12}R^{13}$ or —NH—C($NH_2$)(=NH), or wherein $R^1$ and $R^3$ together is an unbranched, saturated alkylene group having two, three, four or five carbon atoms and thus, together with the adjacent nitrogen atom and carbon atom of the thiadiazine ring system, is a ring having four, five, six or seven ring members, $R^4$ is a hydrogen atom, a lower alkyl group or an aryl-lower-alkyl group, $R^5$ is a hydrogen atom or a lower alkyl group, $R^6$ is a hydrogen atom, a lower alkyl group, an aryl group, a heteroaryl group or an aryl-lower-alkyl group, $R^7$, $R^8$, $R^9$, $R^{10}$, $R^{11}$, $R^{12}$, and $R^{13}$ independently of one another is a hydrogen atom, a lower alkyl group, an aryl group or an aryl-lower-alkyl group, and salts thereof with the physiologically acceptable acids and bases, further wherein the aryl group is a phenyl group, a 1-naphthyl group or a 2-naphthyl group, each of which is optionally substituted by one, two or three identical or different substituents selected from the group of halogen atoms, hydroxyl groups, lower alkyl groups, lower alkyloxy groups, carboxyl groups, lower alkyloxycarbonyl groups, nitro groups, sulfo groups, trifluoromethyl groups or hydrogen-atom- or lower-alkyl-group-substituted amino groups, and the heteroaryl group selected from furanyl groups, thienyl groups, pyrrolyl groups, pyrazolyl groups, imidazolyl groups, triazolyl groups, thiazolyl groups, oxazolyl groups, isothiazolyl groups, isoxazolyl groups, thiadiazolyl groups, pyridyl groups, pyrimidyl groups, pyrazinyl groups, triazinyl groups, benzofuranyl groups, benzothienyl groups, indolyl groups, benzoxazolyl groups, benzothiazolyl groups, benzimidazolyl groups, quinolinyl groups or isoquinolinyl groups, it being possible for the abovementioned groups to be linked to the basic structure of the compounds of the general formula I via any ring carbon atom and it being possible for the abovementioned rings to be optionally substituted by one or two identical or different substituents selected from the group of halogen atoms, hydroxyl groups, lower alkyl groups, lower alkyloxy groups, carboxyl groups, lower alkyloxycarbonyl groups, nitro groups, sulfo groups, trifluoromethyl groups or hydrogen-atom or lower-alkyl-group-substituted amino groups, and the aryl-lower-alkyl group is a methyl group or an ethyl group which is substituted by an aryl group, and the lower alkyl group, or the "lower alkyl" in connection with lower alkyloxy group or lower alkyloxycarbonyl group is an unbranched or branched saturated hydrocarbon group having up to six carbon atoms.

2. Compounds according to claim 1, wherein $R^2$ is a hydrogen atom.

3. Compounds according to claim 2, wherein $R^1$ and $R^3$ together form an unbranched, saturated alkylene group having two, three, four or five carbon atoms and in this way together with the adjacent nitrogen atom and carbon atom of the thiadiazine ring system form a ring having four, five, six or seven ring members.

4. Compounds according to claim 2, wherein $R^6$ is an aryl group.

5. Compounds according to claim 2, wherein $R^6$ is a heteroaryl group.

6. Compounds according to claim 3, wherein $R^1$ and $R^3$ together is a propylene group and in this way together with the adjacent nitrogen atom and carbon atom of the thiadiazine ring system form a pyrrolidine ring.

7. Compounds according to claim 6, wherein $R^6$ is an aryl group.

8. Compounds according to claim 6, wherein $R^6$ is a heteroaryl group.

9. Compounds according to claim 4, wherein $R^6$ is a phenyl group, 2-methylphenyl group, 4-methylphenyl group, 2-methoxyphenyl group, 4-methoxyphenyl group, 2-methoxy-5-methyl group, 2,3-dimethoxyphenyl group, 2,4-dimethoxyphenyl group, 2,5-dimethoxyphenyl group, 2,6-dimethoxyphenyl group, 3,4-dimethoxyphenyl group, 3,5-dimethoxyphenyl group, 2-ethoxyphenyl group, 4-ethoxyphenyl group, 2-chlorophenyl group, 1-chlorophenyl group, 2,4-dichlorophenyl group, 2,6-dichlorophenyl group, 2-fluorophenyl group, 4-fluorophenyl group or 3-trifluoromethylphenyl group.

10. Compounds according to claim 5, wherein $R^6$ is a 2-pyridyl group, a 2-thiazolyl group, a 5-methyl-2-thiazolyl group or a 5-methyl-3-isoxazolyl group.

11. Compounds according to claim 8, wherein $R^6$ is a 2-pyridyl group, a 2-thiazolyl group, a 5-methyl-2-thiazolyl group or a 5-methyl-3-isoxazolyl group.

12. Compounds according to claim 7, wherein $R^6$ is a phenyl group, 2-methylphenyl group, 4-methylphenyl group, 2-methoxyphenyl group, 4-methoxyphenyl group, 2-methoxy-5-methyl group, 2,3-dimethoxyphenyl group, 2,4-dimethoxyphenyl group, 2,5-dimethoxyphenyl group, 2,6-dimethoxyphenyl group, 3,4-dimethoxyphenyl group, 3,5-dimethoxyphenyl group, 2-ethoxyphenyl group, 4-ethoxyphenyl group, 2-chlorophenyl group, 4-chlorophenyl group, 2,4-dichlorophenyl group, 2,6-dichlorophenyl group, 2-fluorophenyl group, 4-fluorophenyl group or 3-trifluoromethylphenyl group.

13. Pharmaceutical composition of matter comprising one or more compounds according to claim 1, and a pharmaceutically acceptable carrier therefor.

* * * * *